United States Patent
Neubauer et al.

(10) Patent No.: US 7,809,184 B2
(45) Date of Patent: Oct. 5, 2010

(54) DEVICES AND METHODS FOR AUTOMATICALLY VERIFYING, CALIBRATING AND SURVEYING INSTRUMENTS FOR COMPUTER-ASSISTED SURGERY

(75) Inventors: Timo Neubauer, Feldkrichen (DE); Norman Plassky, Erfurt (DE)

(73) Assignee: BrainLAB AG, Feldkirchen (DE)

( * ) Notice: Subject to any disclaimer, the term of this patent is extended or adjusted under 35 U.S.C. 154(b) by 1189 days.

(21) Appl. No.: 11/381,584

(22) Filed: May 4, 2006

(65) Prior Publication Data
US 2006/0264742 A1 Nov. 23, 2006

Related U.S. Application Data

(60) Provisional application No. 60/701,567, filed on Jul. 22, 2005.

(30) Foreign Application Priority Data
May 4, 2005 (EP) .................................. 05009785

(51) Int. Cl.
*G06K 9/00* (2006.01)
*A61B 5/05* (2006.01)
(52) U.S. Cl. ..................... 382/154; 382/128; 600/426; 600/424; 600/429
(58) Field of Classification Search ................ 382/154, 382/313, 128; 600/426, 424, 707, 429; 606/130; 340/990, 961; 342/29
See application file for complete search history.

(56) References Cited

U.S. PATENT DOCUMENTS

| 6,535,756 | B1 * | 3/2003 | Simon et al. ............... 600/424 |
| 6,973,202 | B2 * | 12/2005 | Mostafavi .................. 382/103 |
| 7,366,562 | B2 * | 4/2008 | Dukesherer et al. ......... 600/424 |
| 7,458,977 | B2 * | 12/2008 | McGinley et al. ........... 606/130 |
| 7,636,595 | B2 * | 12/2009 | Marquart et al. ............ 600/424 |
| 2004/0039402 | A1 | 2/2004 | Zeiss et al. |
| 2004/0171924 | A1 | 9/2004 | Mire et al. |
| 2004/0181144 | A1 | 9/2004 | Cinquin et al. |

FOREIGN PATENT DOCUMENTS

| WO | 97/29710 | 8/1997 |
| WO | 01/67979 A1 | 9/2001 |

* cited by examiner

*Primary Examiner*—Sheela C Chawan
(74) *Attorney, Agent, or Firm*—Renner, Otto, Boisselle & Sklar, LLP

(57) ABSTRACT

A device and method for automatically verifying, calibrating and surveying a navigable surgical instrument, wherein by means of a scanning device, the geometry of the instrument, in particular the shape of the functional elements (e.g., tips) and their spatial position with respect to an attachable reference system, are detected. By means of a data processing unit, a three-dimensional model of the instrument is calculated from the detected information concerning the geometry of the instrument including the reference system, wherein verification, calibration or surveying is performed with the aid of the ascertained information concerning the geometry of the instrument.

27 Claims, 4 Drawing Sheets

DEVICES AND METHODS FOR AUTOMATICALLY VERIFYING, CALIBRATING AND SURVEYING INSTRUMENTS FOR COMPUTER-ASSISTED SURGERY

RELATED APPLICATION DATA

This application claims priority of U.S. Provisional Application No. 60/701,567 filed on Jul. 22, 2005, which is incorporated herein by reference in its entirety.

FIELD OF THE INVENTION

The present invention relates to devices and methods for automatically verifying, calibrating and surveying instruments for use in computer-assisted surgery, wherein the geometry of the instrument and of a reference system formed by at least two markers and mountable permanently or detachably on the instrument, can be ascertained as a three-dimensional model with the aid of optical scanning methods and then further used by the navigation system. The precision and therefore speed of the scanning process is decisively controlled by the information which is already available and accessible for this instrument, wherein at least one verification, or for that matter a calibration or even a complete survey of the properties of the instrument, can or even has to be carried out.

BACKGROUND OF THE INVENTION

In computer-assisted operations, the position and orientation of surgical instruments with reference to the patient's anatomical structures are represented to the surgeon with the aid of a navigation system (e.g., on the navigation system's display device). In addition to the anatomical structures, the instruments used in the surgical procedure also are trackable using suitable reference systems, which enable precise representation of the instrument. This usually is achieved via active or passive marker structures that disclose their position in the field of operation to the navigation system by emitting or reflecting infrared radiation.

In a registration process, the anatomical structures are initially correlated with reference systems mounted on them via navigable pointers, and are thus spatially trackable by the navigation system in the subsequent operation process. The same is required for the instruments and their reference systems, wherein the instrument functional elements are particularly important. These are surfaces of tools (e.g., cutting edges, tips, etc.) which, for example, can be used to treat bone structures, wherein the surgeon employs a navigation system to obtain precise information concerning the position and orientation of the bone structures, despite possible impaired visibility. Representing the spatial position of the instrument and its functional elements on the display device is based on a correlation of stored geometric data of the instrument, and the spatial data can be ascertained by the navigation system via the reference system attached to the instrument. As soon as the stored geometric data, which mainly describe the functional elements in relation to the reference system, deviate from the actual geometry of the instrument (e.g., after the instrument has been damaged), this inevitably leads to an incorrect representation of the relation between the actual instrument and the anatomical structure to be treated (if the information stored in the database concerning the initial outline of the instrument continues to be used).

Currently, the relation between the functional element of the instrument and its reference system is established once on the basis of manufacturing documents, wherein their compliance is ensured by surveying after the manufacturing process. The relation is stored in the navigation system and is retrieved and used for subsequent operations. These so-called pre-calibrated instruments (e.g., bore guides) are occasionally verified pre-operatively using navigable aids to confirm that they are dimensionally accurate. If they are not sufficiently accurate, this is displayed to the user who should then avoid using the instrument (assuming a calibration as described below is not possible). Matching the model data to the actual existing, possibly deviating instrument is not possible in verification. The precision which verification can achieve is inevitably dependent on the precision of the navigation system, since the respective reference systems are again correlated with each other. Visibility problems and occasionally poor manageability when simultaneously positioning the instrument and the aid tend to extend the operation time.

In another method, a calibration procedure of the instrument is carried out before the instrument is used. The values of functionally relevant parameters of the instrument (length, diameter, etc.) required for navigation but still unset, or unset values for assigning the reference system to the functional element (e.g., socket driver with variable sockets) or the deviations of the actual instrument from the model stored in the database are determined by means of a navigable calibration tool, temporarily or permanently saved in the navigation system and retrieved as needed. Here, too, the visibility and manageability problems described above have a negative effect on the operation time. Calibration functions well for instruments having functional elements with simple geometries, but again only within the limits of the precision which the navigation system can achieve.

Completely surveying functionally relevant structures of an instrument that is difficult to calibrate or verify represents a third method which, however, is not currently employed, since suitable aids are not available, nor could the procedures required be carried out by the operating staff within a justifiable time frame.

SUMMARY OF THE INVENTION

The present invention provides methods and devices for verifying, calibrating and surveying instruments for computer-assisted surgery that allow increased reliability in processes and occasional time reduction when employing navigated instruments for surgical procedures. Further, applicability is not limited to symmetrical or otherwise geometrically simple navigable instruments, but rather instruments with complex geometries also can be prepared for use in computer-assisted surgery.

Verifying, calibrating and surveying serve to provide correct instrument data concerning the geometry of the functional elements and the reference system, and their relation to each other, to the navigation system. This information can be provided before the operation is started, and can be temporarily or permanently stored in the memory of the navigation system, for example. Also, intra-operative application of verifying, calibrating and surveying also can be performed, in order to reuse instruments that have been deformed after carrying out the surgical procedure.

The instrument data can contain specifications regarding the position of the functional elements of the instrument (e.g., instrument tip) in relation to a reference system that is fixedly attached or detachable and formed from markers (e.g., active or passive technology). The data also can specify how the functional elements, such as, for example, the tips of the instrument, are shaped.

In the methods for automatically verifying, calibrating or surveying a navigable instrument, the geometry of the instrument, including a mounted or mountable reference system formed from at least two markers, can be ascertained by means of a scanning device or sensing device, which preferably operates without contact. The data can be compared with previously stored values and can be clearly assigned to the instrument or group of instruments, and/or are newly stored if surveyed. In particular, the reference system or the markers can be arranged permanently on the instrument or can be temporarily attached, e.g., during the scanning procedure. The surface data of the instrument gained by scanning then can be converted by means of a data processing unit or computing unit into a three-dimensional model of the instrument, on the basis of which the instrument-typical parameters can be calculated. The three-dimensional model of the instrument can then contain all the information necessary for navigation, information concerning the geometry of the instrument's functional elements and reference system, and their relation to one another. The geometric information concerning the instrument can be transferred to the navigation system in order to enable the surgeon to use the instrument in computer-assisted surgery.

The devices for automatically verifying, calibrating and surveying navigable surgical instruments are described below.

Scanning Device

The scanning device, which can be integrated in the casing of the navigation system or accommodated in a separate casing, can use known 3D scanning techniques. For example, split beam methods or object screen methods, which require a screened instrument surface, or grid projection methods in which telecentric grids are projected onto the instrument's surface can be used. The scanning unit located in the scanning device preferably operates optically, such as by means of a laser, wherein the instrument surface (including the permanently or detachably mounted reference system) can be sensed. The instrument to be scanned can be mounted in an instrument holder contained in the scanning device, wherein during the scanning procedure, the instrument holder can be moved or rotated relative to the scanning unit in order to make the instrument scanned by the scanning unit accessible from all sides and, thus, enable complete digitization of the surface. Alternatively, the scanning unit can move or rotate relative to a fixed instrument holder. In both cases, the movement or rotations can be detected or controlled via suitable sensor technology integrated in the scanning device, in order to clearly correlate the angular positions with the scanning results, whereby a realistic 3D model can be calculated.

Marker Inspection Unit

An emission model and/or reflection model of the active and/or passive markers forming the reference system can be additionally determined during the scanning procedure by means of an infrared camera unit. The camera unit can be provided separately or can be contained in the scanning device, wherein the position of the camera unit in relation to the scanning unit can be fixed and known or can be ascertained. The information thus ascertained concerning the markers' radiation properties depending on the angle of observation and the resulting optical outline, which may be detected by the navigation system, as the spatial position of the reference system, can be correlated with the results from determining its geometric outline (by means of a scanning process). Thus, observation errors of the navigation system that can result from changing visibility properties of the markers in certain positions, e.g., through partial damage to the markers, can be compensated while the instrument is being used in an operation. This can increase the representation precision of the instrument's position in relation to the anatomical structure to be treated on the display device of the navigation system. In other words, misinterpretations of the spatial position of the reference system, occurring due to damaged markers, for example, can be compensated by the camera unit of the navigation system in the later navigation procedure, and the realistic position of the instrument, in particular of the functional element(s), in relation to the anatomical structure can be calculated and represented.

Data Processing Unit

The device for automatically verifying, calibrating and surveying a navigable instrument can further include a computing unit or data processing unit that can be integrated into the scanning device. Additionally, the computing unit or data processing unit can be linked wirelessly or via a wired connection to the scanning device, forming a separate unit that can communicate with the scanning device. The data concerning the geometry of the navigable instrument, detected by the scanning unit, can be transmitted to and further processed in the data processing unit, e.g., by the data processing unit calculating a three-dimensional model of the instrument (including the reference system) from the results of the surface scan. Preferably, the data processing unit can evaluate the captured data or the three-dimensional model produced, such that the geometry of the instrument's functional elements (e.g., tips) and their position in relation to the reference system of the instrument can be ascertained.

Database

The device can further include a database that can be linked to the data processing unit such that data input into the data processing unit or transmitted to the data processing unit can be saved in the database, for example. Information concerning the geometry of the functional units and of the instrument's reference system, and their position with respect to each other (for various instruments) can be saved to the database from the data processing unit, as can information concerning the quality of the markers or the properties of the emission model and/or reflection model of the instrument-specific reference system.

Display Device

A display device, such as a screen, that communicates via a wired connection or wirelessly (e.g., WLAN or Bluetooth) with the data processing unit and the user interface unit, also can be provided in the device. The ascertained information concerning the geometry of the functional elements of the instrument and of its reference system, and their position with respect to each other, can be represented graphically or in the form of values (e.g., numerical values). Preferably, the three-dimensional model of the instrument, read from the database or ascertained by processing the scanning results, can be displayed on the display device, wherein a substantially exact model can be represented on the display device.

The realistic representation of the three-dimensional model on the display device allows the user to convey commands for correctly carrying out the method to the data processing unit using a user interface unit that is preferably arranged on the display device (e.g., a touch screen). If, after having introduced the instrument into the scanning device, the instrument is not correctly or at all recognized, these commands can control the selection of the correct model from a plurality of similar model variants. Furthermore, the graphical representation of instruments hitherto unknown to the scanning device, possible after a rough scan, can be used to interactively select the areas of the instrument required for successfully preparing the instrument by surveying, in particular the functional elements and the reference system. Designations also can be input for new instruments, making them easier to locating later in the database.

Navigation System Connection

A navigation system also can be linked wirelessly or via a wired connection to the scanning device or data processing unit, such that the information ascertained in accordance with the methods discussed herein (e.g., information concerning the geometry of the functional elements and of the reference system of the instrument, and their position with respect to each other, and also the quality of the active and/or passive markers and their resulting emission model and/or reflection model) can be transferred to the navigation system, in particular to its database. By means of the information, the navigation system can assist the surgeon in carrying out computer-assisted surgery by providing the previously or just ascertained or most current instrument-specific data.

Method for Automatically Verifying, Calibrating and Surveying Navigable Surgical Instruments The method for examining, in particular for automatically verifying, calibrating and surveying, navigable surgical instruments is described in more detail below.

Verification

In verification, the geometric data of the instrument can be advantageously stored in a database of the navigation system. Verifying these instruments involves checking whether the stored data match the actual geometry (e.g., the shape of the functional elements) and their relation to the reference system. Omitting verification can lead to the operation being performed with an instrument that is damaged, wherein the damage is not necessarily obvious. Thus, the position of the instrument may not be correctly represented by the navigation system in relation to the anatomical structure.

Preferably, the navigation system can identify the used instruments on the basis of the characteristic and differentiable spatial arrangement of the markers forming the reference system which, once recognition is successful, enables the instrument-specific data to be retrieved from the database for further use during navigation.

Since the scanning device for carrying out verification can but need not be located in the camera system's field of vision, and identification with the aid of the navigation system cannot therefore be ensured, it is occasionally useful to suggest other identification procedures that enable the scanning device to systematically retrieve the instrument data. Automatically verifying navigable surgical instruments can include identifying an instrument by means of a barcode, NFC (near field communication) or RFID (radio frequency identification), wherein the information media can be automatically detected when inserting the instrument into the scanning device. These mobile information memories can either contain the geometric data of the instrument themselves or can provide the necessary instrument information, on the basis of which it is possible to quickly locate the instrument-specific data in the database of the navigation system.

It is further conceivable for the user to choose the instrument to be verified, using a suitable, in particular graphic interface that can be represented with the aid of the display device of the navigation system or via a display device belonging to the scanning device, for example. The information concerning the instrument, required for locating the geometric data stored in the database, can equally be transferred to the scanning device via a manual input, e.g., by means of an instrument identification code.

Verification is also possible by carrying out an initial scan or rough scan at a reduced level of detail after the instrument has been inserted into the scanning device. The scan can ascertain a model of the instrument at a low or reduced resolution or a rough structure of the instrument in a short time, wherein the model or structure allows the instrument to be searched for by comparison with instrument models stored in the database. Here, too, once the search is successful, the complete instrument data saved in the database of the navigation system can be read and used in the subsequent verification. It is also possible, after the rough scan of the instrument, to carry out a fine scan or a further or second scanning procedure of the instrument or parts thereof at a higher or increased level of detail, from which a model at a high or higher resolution or a detailed or more precise structure can be ascertained.

For all the described verification variants, it is advantageous, after identifying the instrument, to scan at least the functional elements and the reference system of the instrument, in particular their shape and position with respect to each other, at a high level of detail to obtain sufficiently precise data for comparing the geometry stored in the database with the actual instrument geometry. Recognition logic then can be used that independently identifies the characteristic instrument elements and can therefore define an instrument reference system on the basis of the markers forming the reference system, for example, and can ascertain the position of the functional elements relating to it. When using passive spherical markers, for example, identifying the reference system is ensured by their easily recognizable shape, which otherwise occurs rather infrequently in surgical instruments. Instruments with active markers, which can be linked to an energy source during the scanning procedure if detecting the emission model is desired, can likewise be formed with geometrically larger characteristic shapes in order to more easily locate the geometrically small diodes in their vicinity (using the recognition logic, once a rough scan has been performed). When using an external energy source linked by cables, the recording device is preferably embodied to be spatially fixed, while the scanning unit moves relative to it.

If the verification result is positive, i.e., the instrument is identical or substantially similar to the stored model within a given tolerance level, the result can be transmitted to the navigation system via a suitable data link (via a wire connection, wirelessly) and the instrument can be activated for the subsequent application.

Calibration

Automatically calibrating navigable surgical instruments can be identical in its requirements and method sequence to verifying as described above. In verification, only one assertion may be made concerning the similarity of the model and the actual instrument, which, if deviated from beyond or to a greater extent than the permitted tolerance level, excludes the instrument from being used in navigation. In calibrating, the geometric information of the instrument saved in the navigation system's database may be corrected such that the instrument can be scanned in the areas beyond the permitted tolerance levels and the results transferred into the database of the navigation system as updated model data.

Surveying

In surveying, it is not necessary for geometric data of the instrument to be previously stored in the database of the navigation system, or for the instrument to be known to the navigation system or the scanning device. Automatically surveying, as in the procedure described above, can begin by mounting the instrument to be surveyed, equipped with passive or active markers, in the instrument holder of the scanning device. The instrument then can be scanned to ascertain a three-dimensional model of the instrument, or an initial scan or rough scan can be performed at a reduced level of detail or low resolution.

After the scan, a rough three-dimensional model of the instrument or an instrument model at a low resolution can be calculated with the aid of the data processing unit and then represented to the user on the display device. By using the recognition logic to locate characteristic shapes, e.g., geometric shapes forming the reference system, the scanning device, after a first evaluation of the geometric data of the initial scan, can provide suggestions to the user for defining the markers forming the reference system and the functional elements of the instrument using colored or other distinctions. The user can confirm the suggestions or make improvements with the aid of the user interface unit, which preferably is embodied as a touch screen. The data processing unit can use these specifications to define the scanning area for the subsequent or second scanning procedure, which in particular can be carried out in the defined areas of the instrument's functional elements and reference system at high or increased precision or resolution. The surface information gained can then be transferred via a wired connection or wirelessly to the data processing unit, which can calculate the exact geometric values for the position of the markers forming the reference system and their distance from the instrument's functional elements (e.g. tips).

The instrument-specific parameters determined in this way can be transferred wirelessly or via a wired connection to the database of the navigation system which, when recognizing the characteristic reference geometry formed by at least two active or passive markers, can read the corresponding information concerning the position of the functional element from the database. In order to later verify or calibrate the instrument, it is conceivable to save the instrument geometry in the database under a name input by the user via the user interface unit, in order to facilitate location at a later time. It is equally conceivable to use a mobile data memory mounted on the instrument, as already mentioned, which uses RFID (radio frequency identification) technology, for example. The geometric information required to later verify or calibrate other scanning devices can then be saved and automatically read on the instrument.

Result of Automatically Verifying, Calibrating and Surveying Instruments for Computer-Assisted Surgery Once navigable surgical instruments have been automatically verified, calibrated and/or surveyed, the spatial position of the instrument's reference system, formed from at least two active or passive markers, can be determined with the aid of the navigation system. The instrument then can be identified from the characteristic position of the markers with respect to each other, and a complete model of the instrument (including the reference system and functional elements) can be loaded from the database of the navigation system, and/or its position in relation to the anatomical structure to be treated can be represented very precisely to the surgeon on the display device of the navigation system.

The invention further provides a computer program which, when loaded onto a computer or running on a computer, carries out the methods as described above. The invention further provides a program storage medium or a computer program product comprising such a program.

The forgoing and other embodiments of the invention are hereinafter discussed with reference to the drawings.

DETAILED DESCRIPTION

Figure 1:
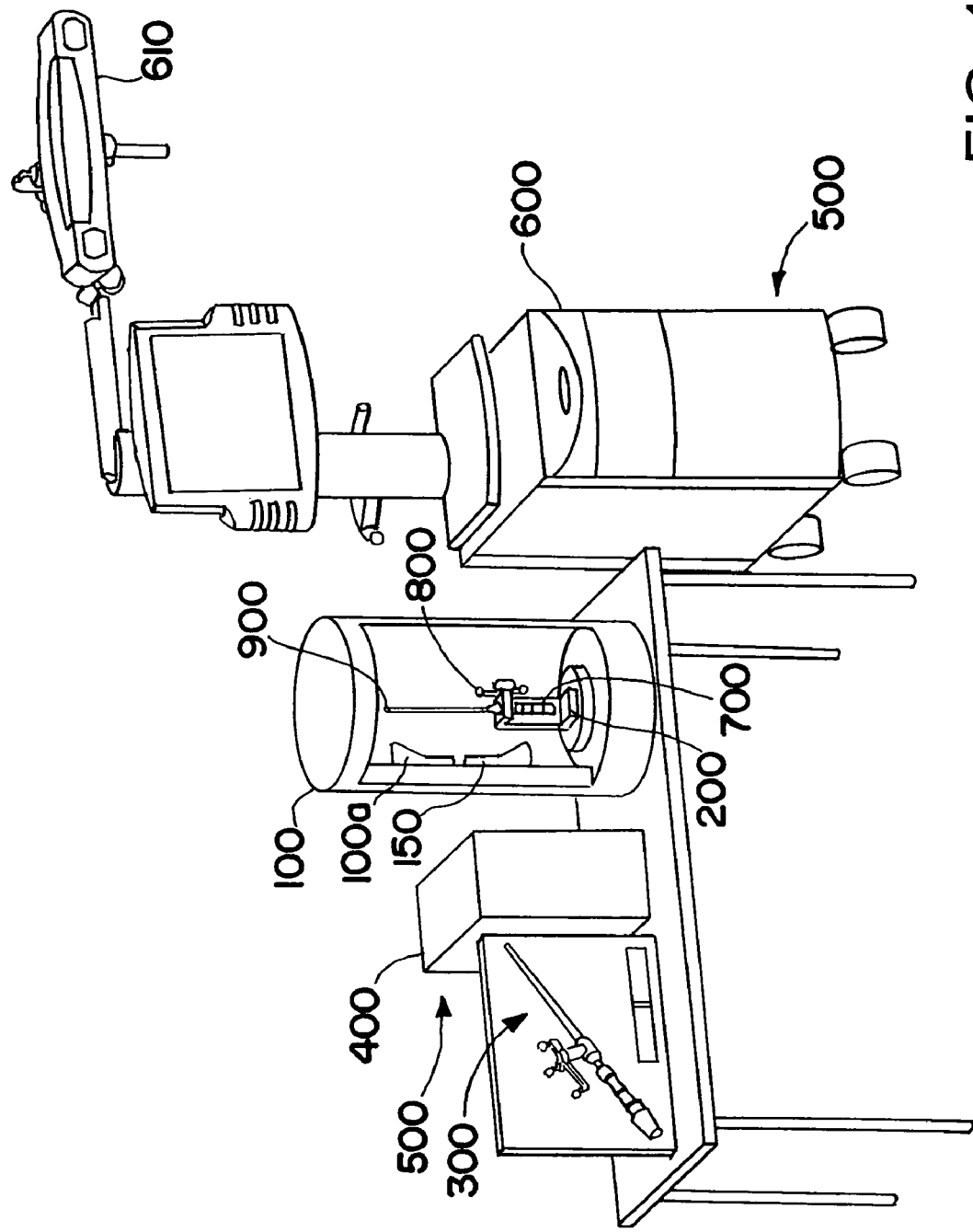
FIG. 1 illustrates an exemplary device for automatically verifying, calibrating and surveying an instrument, with a separate display device and a separate data processing unit in accordance with the invention.

FIG. 1 shows an exemplary device for automatically verifying, calibrating and surveying an instrument, wherein a scanning device 100 and an instrument holding unit 200 are arranged in a cylindrical casing. An infrared camera unit 150 also can be attached in the casing for checking the condition, shape and/or quality of active or passive markers. For example, infrared radiation can be emitted onto the markers and the infrared camera unit 150 can detect the reflected infrared radiation. Alternatively, the infrared camera unit 150 can detect infrared radiation emitted by the markers. In the present example, the instrument 700 is positioned within the casing, preferably fixedly or non-movably in the instrument holding unit 200, wherein a reference system 800 is attached to the instrument 700, and the instrument 700 includes an instrument tip 900 as a functional element.

The scanning device 100 preferably senses the instrument optically, for example, by means of a laser or tactilely, wherein the casing of the scanning device 100 can be open, as in the present example, or also closed. The scanning device 100 or the laser of the scanning device 100 also can perform a rotation about the instrument 700, or the scanning device 100 or the casing of the scanning device 100 can be formed such that a rotation of the instrument holding unit 200 or of the instrument 700 can be performed and the shape of the instrument 700 can be detected from all sides. The casing of the scanning device 100 exhibits a size, on the basis of which conventional operation instruments can be positioned in the casing of the scanning device 100 and preferably are completely sensed. The infrared camera unit 150, which in the present example is attached in or on the casing of the scanning device 100, can examine the quality and, in particular, the uniform reflection properties of the markers of the reference system 800. This can be accomplished, for example, by the infrared camera unit 150 irradiating the markers from various angles and by ascertaining the condition or quality which the markers exhibit from the reflection characteristics of the markers. Thus, for example, uniform reflection properties of the markers can indicate a good or intact condition or a high quality of the markers, whereas non-uniform reflection properties or non-uniform reflection characteristics, as detected by the infrared camera unit 150, can indicate a damaged condition or low quality of the markers.

From the quality ascertained, the condition or shape of the markers and/or of the reference system 800, detected from various angles of observation by means of the infrared camera unit, for example, the optical outline of the reference system 800 or of the markers can be calculated. The calculated outline can be combined with the ascertained information concerning the geometric outline of the reference system 800. The correlation of the optical and geometric outlines can be used to compensate for errors by a camera 610 of the navigation system 600 during navigation, depending on the angle of observation of the reference system 800, due to the spatial position being incorrectly calculated because of damaged markers, for example.

The detected information concerning the instrument 700 and the reference system 800, which is preferably arranged on the instrument 700 during the scanning procedure, and the position or quality of the markers, can be transferred from the scanning device 100 to a data processing unit 400 in which the captured scanning data are converted into a virtual model. The data processing unit 400 can recognize or ascertain functional elements or functional units of the instrument 700, for example, directly from the captured data concerning the geometry of the instrument 700 and the reference system 800. Alternatively, the data processing unit 400 can ascertain the corresponding functional elements, taking into account the geometrical relations of the instrument 700, such as the characteristic arrangement of the markers forming the reference system 800, for example, by comparing the ascertained geometric relations with the geometric relations saved in a database.

The database, in which the comparative values or comparative geometric relations or newly ascertained geometric relations can be saved, can be arranged in the data processing unit 400. The virtual three-dimensional model of the instrument 700, calculated by the data processing unit 400, or the ascertained information concerning the geometry of the instrument 700 and the reference system 800, can be displayed or graphically represented on a display device 300, such as a touch screen, for example.

In particular, various alternative shapes or geometries of the instrument 700 or of the functional elements of the instrument 700 also can be displayed, the shape or geometry of which is similar to the ascertained geometries or functional units of the instrument, from which a user can choose an instrument 700 or a functional element. The information ascertained, such as the geometric relations of the instrument 700 and the reference system 800 or the virtual model of the instrument 700, can be transferred from the data processing unit 400 to the navigation system 600 via a wired connection or wirelessly, such as by means of WLAN or Bluetooth, via a communication unit 500 that can be arranged on or in the data processing unit 400 and navigation system 600, such that a navigation procedure can be carried out by the navigation system 600 on the basis of the ascertained information concerning the geometry of the instrument 700. In the navigation procedure, the ascertained information concerning the geometry of the instrument 700 and the reference system 800 can be taken into account, and information concerning the condition or quality of the markers also can be taken into account, such that damage to the markers or changes in the geometry or damage to the instrument, for example, can be taken into account in the navigation procedure, in order to guarantee a precise navigation procedure.

Figure 2:
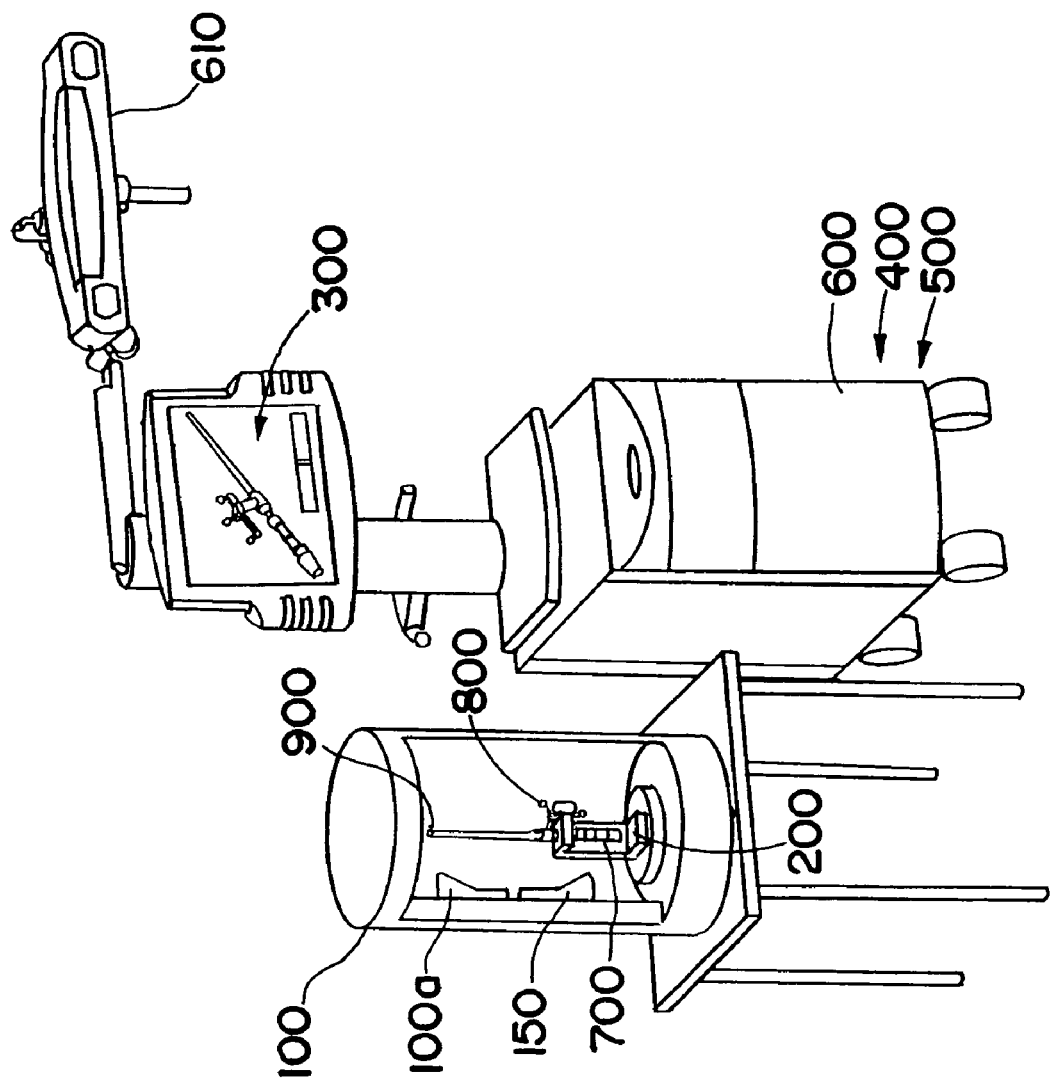
FIG. 2 illustrates another exemplary device for automatically verifying, calibrating and surveying an instrument, with a display device attached to a navigation system, and a data processing unit integrated into the navigation system in accordance with the invention.

FIG. 2 shows another exemplary device for automatically verifying, wherein the data processing unit 400 is integrated into the navigation system 600 and/or arranged in the navigation system, and the display device 300 is integrated into the navigation system 600 and/or arranged on the navigation system 600.

Figure 3:
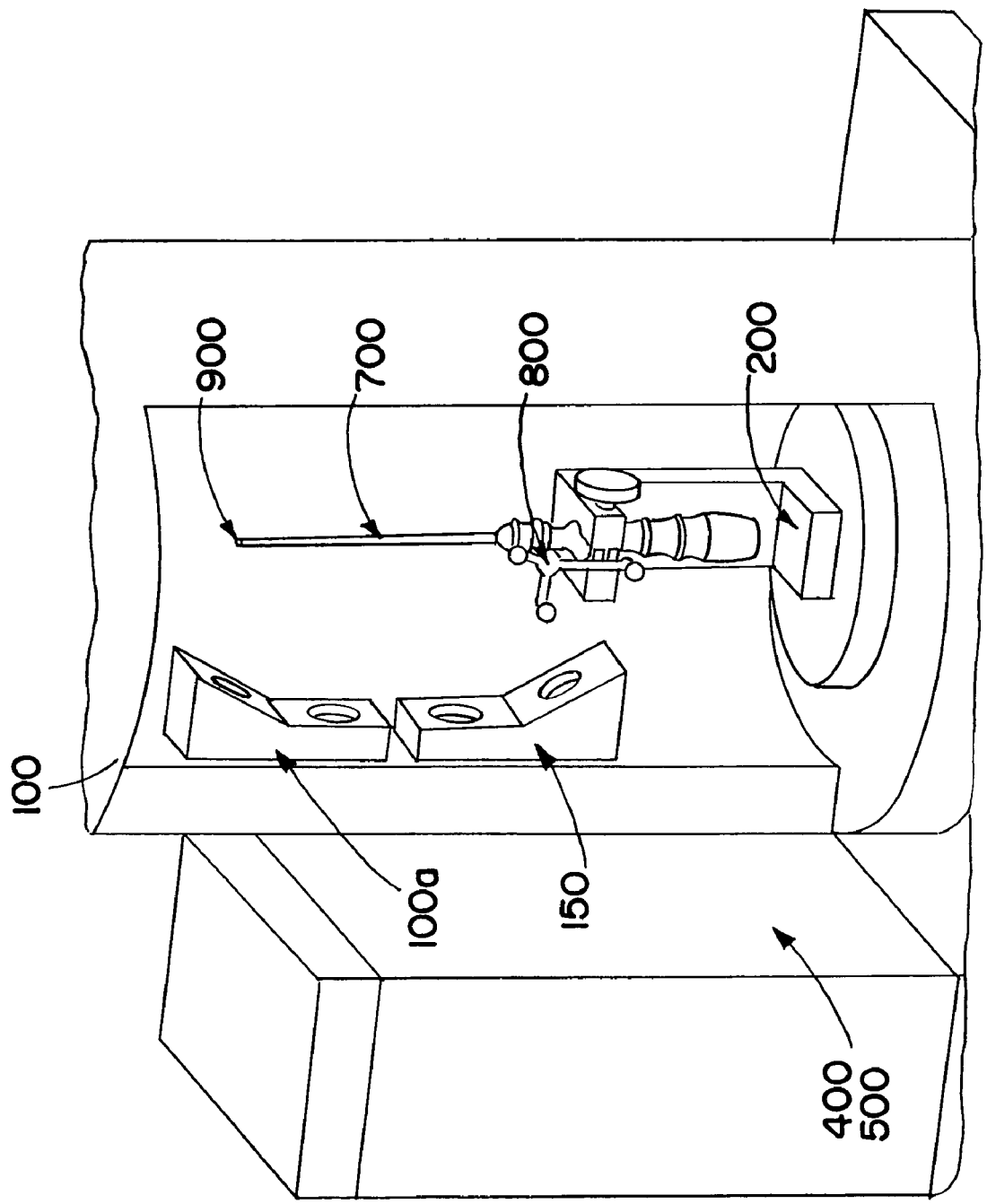
FIG. 3 illustrates an exemplary scanning device in accordance with the invention, with the instrument to be prepared.

FIG. 3 shows a casing of the scanning device 100 in which the instrument 700 is positioned, including a scanning unit 100*a*, an infrared camera unit 150 and an instrument holder 200 in which the instrument 700 is positioned, preferably fixedly. The instrument 700 has an instrument tip 900 as a functional element, the shape of which can be detected by the scanning unit 100*a*, for example. A reference system 800 also is arranged on the instrument 700, the shape of which can be detected by the scanning unit 100*a*, for example, wherein the reference system 800 is formed by markers. The reflection characteristics of the markers can be detected by the infrared camera unit 150, for example.

Figure 4:
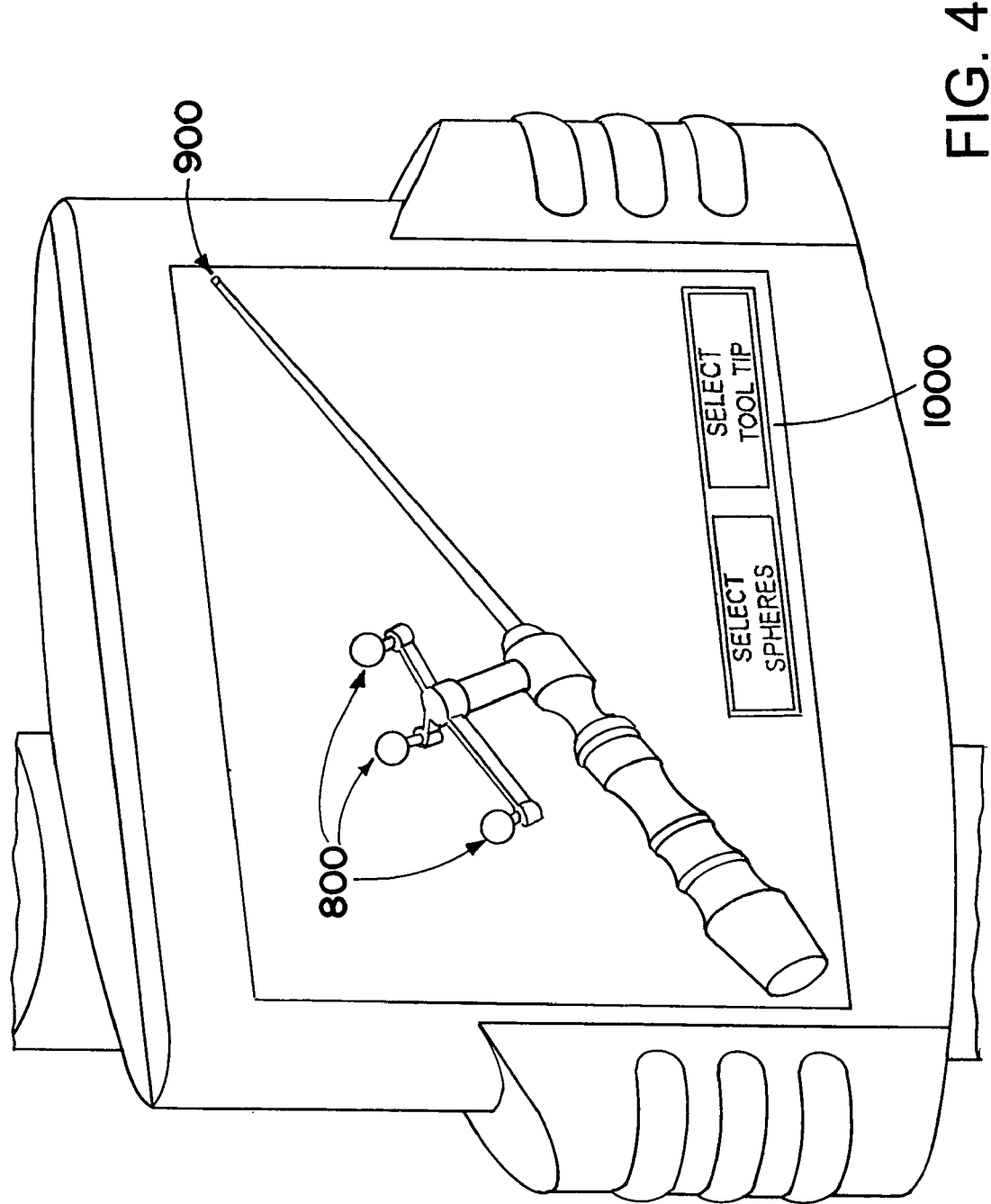
FIG. 4 illustrates an exemplary display device in accordance with the invention.

FIG. 4 represents the display device 300 which graphically represents the virtual ascertained three-dimensional model of the instrument 700 together with the reference system 800. By means of a user interface unit 1000, preferably arranged on the display device 300, the markers or functional elements, such as the tip 900 of the instrument, can be selected by a user, for example.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for automatically verifying, calibrating or surveying an instrument, said instrument including a reference system, the method comprising:

detecting a geometry of i) the instrument and ii) the reference system based on a scan of the instrument and the reference system;

calculating a three-dimensional model of the instrument based on the detected geometry of the instrument and the reference system;

verifying, calibrating or surveying the instrument based on the geometry of the three-dimensional model;

recording, via a camera unit, emission characteristics and/or reflection characteristics of the reference system from different angles of observation;

ascertaining from the emission characteristics and/or reflection characteristics a quality, condition or shape of the reference system or of individual markers of the reference system based on the angle of observation;

calculating an optical outline of the reference system from the ascertained quality, condition or shape of the reference system and/or of the individual markers of the reference system; and combining the optical outline of the reference system with the ascertained quality, condition or shape of the reference system or with the individual markers of the reference system.

2. The method of claim 1, wherein said reference system is formed by at least two active or passive markers.

3. The method of claim 1, wherein calculating includes using a data processing unit to perform the calculations.

4. The method of claim 1, wherein verifying or calibrating comprises:
recognizing the geometry of the reference system or the geometry of a functional element of the instrument;
comparing at least one of the recognized geometry of the reference system or the recognized geometry of the functional element with data corresponding to geometries of functional elements and/or reference systems of other instruments, wherein said data is stored in memory; and
automatically retrieving information stored in memory for the instrument based on the comparison.

5. The method of claim 1, further comprising:
detecting a surface of the instrument via the scan; and
representing the detected surface on a display device as a three-dimensional model of the instrument, such that a functional element and the reference system of the instrument can be selected by a user via a user interface unit.

6. The method of claim 5, wherein detecting the surface includes detecting the reference system and a functional element of the instrument.

7. The method of claim 1, wherein if a deviation between the detected geometry of the instrument and geometric data stored in memory is less than or equal to a predetermined tolerance level, the instrument being examined and the geometric data stored in memory are assumed to match and a positive verification result is transmitted to a navigation system, whereupon navigation of the instrument is activated for a subsequent application.

8. The method of claim 1, wherein detecting a geometry comprises:
calculating a distance between a functional element of the instrument and the reference system;
transmitting the calculated distance to a navigation system.

9. The method of claim 1, further comprising detecting data corresponding to a surface of the instrument as the instrument is rotated about a scanning unit, wherein the three dimensional model of the instrument is calculated using the detected surface and rotation data.

10. A method for navigating an instrument, comprising:
verifying, calibrating or surveying the instrument according to claim 1;
detecting a spatial position of the reference system;
determining a spatial position of a functional element of the instrument based on geometric data regarding the reference system, said data stored in computer memory; and
providing on a display the spatial position of the functional element relative to an anatomical structure to be treated.

11. A non-transitory computer readable medium comprising computer executable instructions adapted to cause a processor to perform the method of claim 1.

12. A method for automatically verifying, calibrating or surveying an instrument, said instrument including a reference system, the method comprising:
detecting a geometry of the instrument and the reference system based on a scan of the instrument and the reference system, wherein detecting comprises
obtaining a first scan of the instrument at a first resolution;
ascertaining a first geometric structure of the of the instrument based on the first scan;
comparing the first geometric structure with geometric data stored in memory; and
retrieving information stored in memory for the instrument based on the comparison;
calculating a three-dimensional model of the instrument based on the detected geometry of the instrument and the reference system; and
verifying, calibrating or surveying the instrument based on the geometry of the three-dimensional model.

13. The method of claim 12, further comprising verifying or calibrating the instrument after the instrument has been identified, wherein verifying or calibrating comprises:
obtaining a second scan of functional elements of the instrument and the reference system at a second resolution, wherein the second resolution is higher than the first resolution;
comparing data from the second scan with geometric data stored in memory, said geometric data relating to the instrument.

14. The method of claim 13, wherein obtaining a second scan includes scanning the shape and position of the functional elements and the reference system with respect to one another.

15. The method of claim 13, wherein calibration comprises correcting geometric instrument data stored in memory when a deviation between the detected instrument geometry and the geometric instrument data stored in memory is greater than a predetermined tolerance level,
wherein said correction is based on the ascertained geometry of the instrument, or said correction is based on data obtained during a new scan of the instrument in areas of the instrument that are not within the predetermined tolerance.

16. A method for automatically verifying, calibrating or surveying an instrument, said instrument including a reference system, the method comprising:
detecting a geometry of the instrument and the reference system based on a scan of the instrument and the reference system;
calculating a three-dimensional model of the instrument based on the detected geometry of the instrument and the reference system; and
verifying, calibrating or surveying the instrument based on the geometry of the three-dimensional model, wherein surveying the instrument comprises
obtaining a first scan of the instrument and reference system at a first resolution;
calculating a three-dimensional model of the instrument from the first scan;
providing the model on a display device;
locating characteristic shapes forming the model;
ascertaining a scan area based on the characteristic shapes; and
obtaining a second scan of the ascertained scan area at a second resolution, wherein the second resolution is higher than the first resolution.

17. The method of claim 16, wherein locating characteristic shapes includes locating geometric shapes of the reference system or a functional element of the instrument.

18. A device for automatically verifying, calibrating or surveying an instrument, comprising:
a scanning unit configured to detect a three-dimensional geometry of the instrument, a three-dimensional geometry of a reference system attachable on the instrument, and the geometry of the reference system relative to the geometry of the instrument, wherein the instrument can be rotated relative to the scanning unit;

an infrared camera unit, wherein a spatial position of the camera unit with respect to the scanning unit is known or can be determined, and wherein the camera unit is operable to determine emission characteristics or reflection characteristics of the reference system and/or markers of the reference system; and a data processing unit communicatively coupled to the scanning unit and the infrared camera unit, the data processing unit configured to calculate a three-dimensional model of the instrument and ascertain a position of a functional element of the instrument, said calculation based on a characteristic arrangement of the reference system, based on the emission or reflection characteristics ascertain a condition, quality or a shape of the reference system or of individual markers of the reference system based on the angle of observation, calculate an optical outline of the reference system from the ascertained quality, condition or shape of the reference system and/or of the individual markers of the reference system, and combine the optical outline of the reference system with the ascertained quality, condition or shape of the reference system or with the individual markers of the reference system.

19. The device of claim 18, further comprising a database, wherein at least one of the detected information concerning the geometry of the instrument and the reference system, information concerning the condition, quality or shape of the markers, information concerning the geometry of other instruments and their reference systems, or information concerning the condition, quality or shape of the markers of other instruments can be saved in the database.

20. The device of claim 19, wherein information concerning the reference system includes a distance from the reference system to a functional element of the instrument.

21. The device of claim 18, further comprising:
a display device on which the ascertained three-dimensional model of the instrument can be represented; and
a user interface unit configured for selecting a functional element of the instrument or the markers forming the reference system.

22. The device of claim 21, wherein the display device is a touch screen, and the user interface is arranged on the touch screen.

23. The device of claim 18, further comprising a navigation system linked wirelessly or via a wired connection to the data processing unit, wherein the ascertained information concerning the instrument can be transmitted to the navigation system, and on the basis of the transferred information concerning the arrangement of the markers forming the reference system, a navigation procedure can be carried out using the navigation system and incorporating and/or compensating for ascertained errors of the markers.

24. The device of claim 18, further comprising a communication device for communicating with an instrument equipped with a mobile, read-only or readable and writeable data memory, wherein identifying features of the instrument are provided to the data processing unit and/or the scanning unit via the communication link.

25. The device of claim 24, wherein the communication device uses wireless transfer technologies.

26. The device of claim 18, further comprising an instrument holder configured to hold the instrument relative to the scanning unit, wherein the instrument holder and scanning unit are configured for relative movement to each other.

27. A program embodied on a non-transitory computer-readable medium for automatically verifying, calibrating or surveying an instrument that includes a reference system, comprising:

code that determines a geometry of i) the instrument and ii) the reference system, said determination based on scan data of the instrument and scan data of the reference system;

code that calculates a three-dimensional model of the instrument based on the detected geometry of the instrument and the reference system; and code that verifies, calibrates or surveys the instrument based on the geometry of the three-dimensional model code that records emission characteristics and/or reflection characteristics of the reference system from different angles of observation;

code that ascertains from the emission characteristics and/or reflection characteristics a quality, condition or shape of the reference system or of individual markers of the reference system based on the angle of observation;

code that calculates an optical outline of the reference system from the ascertained quality, condition or shape of the reference system and/or of the individual markers of the reference system; and code that combines the optical outline of the reference system with the ascertained quality, condition or shape of the reference system or with the individual markers of the reference system.

* * * * *